United States Patent [19]

Greenberg et al.

[11] 4,158,051
[45] Jun. 12, 1979

[54] PET COLLAR

[75] Inventors: Jack Greenberg; Grover D. Cloyd, both of Richmond, Va.

[73] Assignee: A. H. Robins Company, Inc., Richmond, Va.

[21] Appl. No.: 865,770

[22] Filed: Dec. 29, 1977

Related U.S. Application Data

[63] Continuation-in-part of Ser. No. 758,271, Jan. 10, 1977, abandoned.

[51] Int. Cl.$^2$ .............................................. A01K 27/00
[52] U.S. Cl. ..................................... 424/28; 119/106; 119/156; 424/16
[58] Field of Search .................... 424/16, 28; 119/106, 119/156

[56] References Cited

U.S. PATENT DOCUMENTS

| | | | |
|---|---|---|---|
| 3,852,416 | 12/1974 | Grubb et al. | 424/14 |
| 3,904,746 | 9/1975 | Aries | 424/28 |
| 3,918,407 | 11/1975 | Greenberg | 119/156 |

FOREIGN PATENT DOCUMENTS 1128219  4/1962  Fed. Rep. of Germany.

OTHER PUBLICATIONS

Matthyse et al., Chem. Abstr. 84:100803s (1976).
Merck Index 9th Ed. Merck & Co. Rahway N.Y. #1790 Carbaryl #3058 Dichlorvos #6178, "Naled " #7625 Propoxur.
CA. 82 #39600p, #94232v, #94143s (1975); 79 #28385j (1973), 66 #1826p (1967).

*Primary Examiner*—Shep K. Rose

[57] ABSTRACT

An improved pet collar for combatting fleas and ticks is disclosed. The pet collar comprises a synthetic resinous matrix material, from about 5 to about 20 weight % of naled (dimethyl 1,2-dibromo-2,2-dichloroethyl phosphate) and from about 2 to about 12 weight % of a substantially non-volatile carbamate.

7 Claims, 3 Drawing Figures

U.S. Patent  Jun. 12, 1979  4,158,051
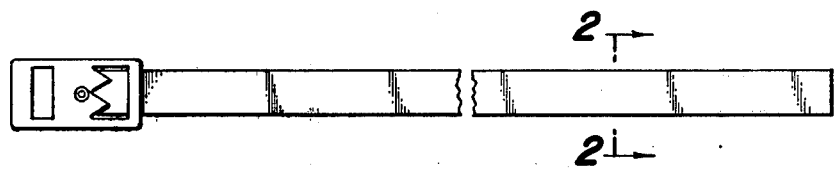
Fig.1
Fig.2
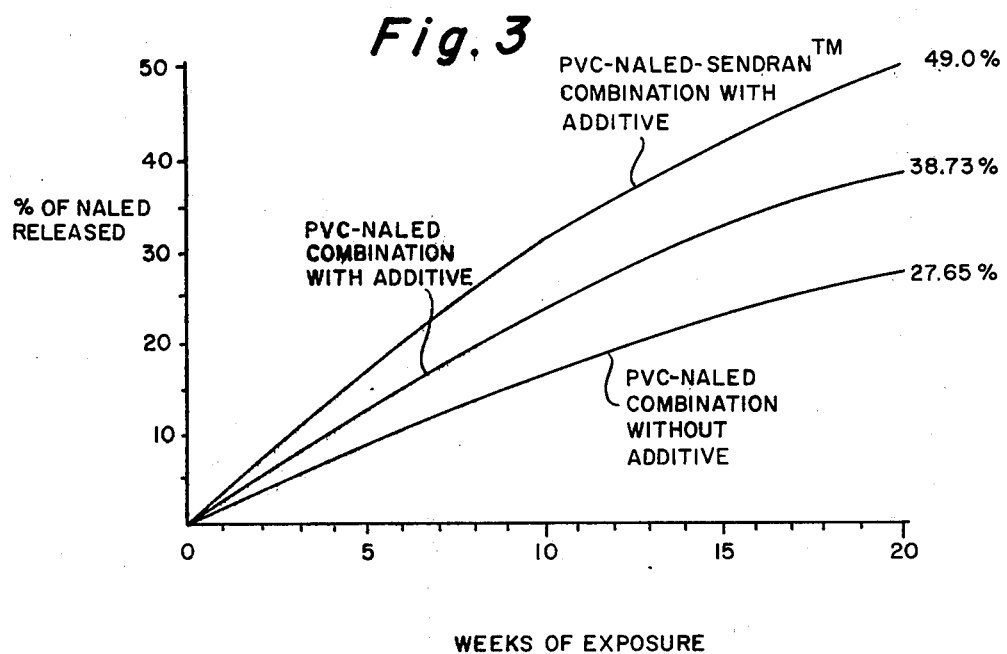
Fig.3

PET COLLAR

This application is a continuation-in-part of Ser. No. 758,271, filed Jan. 10, 1977 now abandoned.

BACKGROUND OF THE INVENTION

1. Field of the Invention

This invention relates to the control of fleas and ticks on warm-blooded animals, such as cats and dogs, by application of a combination insecticidal gas and powder generator device. More particularly, this invention relates to novel compositions and to methods of manufacture of a pet collar comprised of a synthetic resin such as polyvinyl chloride (PVC) having dispersed therein the insecticide dimethyl 1,2-dibromo-2,2-dichloroethyl phosphate, commonly known as naled, and a substantially non-volatile carbamate.

2. Discussion of the Prior Art

Heretofore, phosphate insecticides such as dimethyl 2,2-dichlorovinyl phosphate commonly known as dichlorvos (DDVP) or by its trademark Vapona, or dimethyl 1,2-dibromo-2,2-dichloroethyl phosphate commonly known as naled, have been widely used for controlling insects. The incorporation of naled and a surface porosity control component in a solid thermoplastic resinous pet collar to control fleas is disclosed in U.S. Pat. No. 3,918,407. The incorporation of 3 to 25% of a substantially non-volatile carbamate in a solid thermoplastic vinylic resin in the form of an animal collar is disclosed in U.S. Pat. No. 3,852,416. German Auslegeschrift No. 1,128,219 alleges that phosphoric acid esters which are ineffective as insecticides when used at standard concentrations, when combined with carbamates, greatly intensify synergetically their effectiveness as insecticides or acaricides. U.S. Pat. No. 3,111,539 discloses various carbamates as being useful insecticides.

SUMMARY OF THE INVENTION

This invention provides resinous compositions in the form of an animal collar which releases naled insecticide and a substantially non-volatile carbamate insecticide over an extended period of up to 120 days to control fleas and ticks on the animal wearing the collar. The cured resinous compositions from which collars are prepared contain initially dissolved or suspended in the interstices thereof from about 5 to about 20 weight % naled and from about 2 to about 12 weight % substantially non-volatile carbamate insecticide.

The present invention is based on the discovery that when naled insecticide, a substantially non-volatile carbamate insecticide and a surface porosity control component are incorporated in a resin matrix the naled insecticide is released from the cured collar at a greater rate than from a cured collar containing only naled, thereby resulting in a more effective collar for the control of fleas and ticks on warm-blooded animals, particularly dogs and cats. The invention is also based on the discovery that naled is emitted from the collar as a vapor and the carbamate migrates from the collar as a powder without affecting the release of each other. Moreover, the carbamate which migrates as a powder onto the surface of the collar is substantially dry and free of liquid naled.

Cured resinous compositions for cats will contain 5 to 12 weight % naled and 2 to 5 weight % carbamate, preferably 7 to 10 weight % naled and 2 to 3.5 weight % carbamate. Cured resinous compositions for dogs will contain 8 to 20 weight % naled and 2 to 12 weight % carbamate, preferably 12 to 17 weight % naled and 3.5 to 8 weight % carbamate.

It is an object of this invention, therefore, to provide a novel effective animal collar.

Another object of this invention is to provide an insect combatting device in the form of a solid composition to be worn as an animal collar which releases naled insecticide and a carbamate insecticide over an extended period of time for effective control of fleas and ticks.

A further object is to provide a resinous composition in the form of an animal collar which provides two types of insecticides which are released as a vapor and a powder respectively.

A still further object of this invention is to provide a method of treating animals by making a strip of synthetic resin containing from about 5 to about 20 weight % naled insecticide and from about 2 to about 12 weight % of a substantially nonvolatile carbamate through the use of a volatile additive which is released during the curing step to produce a texture including porous surface openings which allow for an unexpectedly large increase in the release of naled gas at a rate effective to control fleas and ticks for a period of up to about 120 days.

These and other objects of the invention will become more fully apparent from the claims, and from the description as it proceeds in connection with the appended drawings wherein:

FIG. 1 is a plan view of a representative pet collar embodying the present invention;

FIG. 2 is a view of the collar in cross section taken along lines 2—2 of FIG. 1;

FIG. 3 is a graph showing the comparative rate of naled release in collars employing naled and Sendran ™ (2-isopropoxyphenyl-N-methyl carbamate) with a surface porosity control component or additive in accordance with the present invention, naled with a surface porosity control component or additive and naled without the additive.

Referring now to the drawings, FIGS. 1 and 2 show a typical collar adapted for pets such as dogs or cats. The components making up a satisfactory naled carbamate-containing pet collar include a synthetic resin that is sufficiently pliable or flexible to be encircled around the animal's neck and has a strength sufficient to remain on the animal throughout a period of at least 4½ months or the period during which naled carbamate is released in amounts effective to control fleas.

The collar constituted a band or strip of a PVC-naled-carbamate combination with the concentration of PVC sufficiently large to give the collar physical properties such as strength, flexibility, and freedom from tackiness to make it suitable for use as a collar for the animal. Normally, the cross-sectional dimensions of the collar vary from about one-fourth to five-eighth inch in width, and from about three thirty-seconds to three-sixteenths inch in thickness. For collars of the present invention employing the PVC-naled-carbamate combination, the preferred dimensions are three-eighth in width and one-eighth inch in thickness, and the cross section is as illustrated in FIG. 2.

The collars are made of sufficient length to encircle the neck of the largest dog or cat to be encountered, and for smaller animals, the end of the collar may be cut off to reduce the size of the collar to correspond with the size of the animal. With the PVC-naled-carbamate combination and dimensions as given above, the perimeter of the collar is about one inch and the mass of the collar is about one gram per lineal inch. By use of a clasp having a friction grip, the collar can be adjustably placed on the animal without the need for holes.

DETAILED DESCRIPTION AND PREFERRED EMBODIMENTS

In accordance with the present invention naled insecticide, a substantially non-volatile carbamate insecticide and a surface porosity control component are incorporated into resin compositions prior to curing. The cured collars release vaporized naled insecticide and powdery carbamate insecticide over an extended period of time for control of fleas and ticks on animals. The collar is comprised of a strip of flexible synthetic resin material containing from about 5 to about 20 weight % naled insecticide and from about 2 to about 12 weight % of a substantially non-volatile carbamate insecticide and having a width, thickness and length sufficient to encircle the neck of the animal with clamping means at one end of the collar for engaging a spaced collar portion to prevent loss of the collar from the neck of the wearing animal.

The strip is formed from plastisol dispersions or dry blend mixtures of a synthetic resin, naled insecticide, carbamate insecticide and a surface porosity control component. Plastisol dispersions may be cured by heating in open faced molds and dry blend mixtures may be extruded with heating to curing temperatures to provide strips of flexible plastic. The compositions are characterized by their provision of the benefits of naled insecticide and a substantially non-volatile carbamate insecticide for control of fleas and ticks on animals. The naled penetrates the atmosphere surrounding the animal as a vapor and the carbamate as it migrates onto the collar surface as a powder is displaced therefrom by rubbing or dusting onto the hair of the animal. The compositions serve as a reservoir providing continuous replenishment of naled insecticide and carbamate insecticide.

The carbamates which can be used in combination with naled in the present invention are represented by the formula:

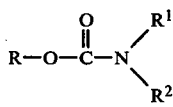

Formula I wherein;

R is phenyl, substituted phenyl, naphthyl, substituted naphthyl, heterocyclic or substituted heterocyclic,
$R^1$ is hydrogen or lower alkyl, and
$R^2$ is lower alkyl.

The term "lower alkyl" as used herein refers to an alkyl radical having one to six carbon atoms. The carbon chains can be straight or branched. The term "lower alkoxy" has the formula —O—lower alkyl. The substituted phenyl radical or the substituted naphthyl radical can have one or more substituents selected from radicals such as lower alkyl, chloro, bromo, fluoro, lower alkoxy, lower alkylamino, lower dialkylamino or lower alkylthio. The preferred number of substituents is one to two. The term "heterocyclic" as used herein refers to a heterocyclic group having an oxygen atom, a sulfur atom or one or two nitrogen atoms in the nucleus thereof. The term "substituted heterocyclic" as used herein refers to a heterocyclic group substituted with one or more groups such as lower alkyl, lower alkoxy, lower alkylthio, lower alkylamino, lower dialkylamino, carbamoyl, alkyl substituted carbamoyl or halogen. The preferred number of substituents is one to two.

Carbamates which can be used in practicing the present invention include:
2-isopropylphenyl-N-methyl carbamate,
2-isopropoxyphenyl-N-methyl carbamate,
3-(1-methylbutyl)phenyl-N-methyl carbamate,
3-(1-ethylpropyl)phenyl-N-methyl carbamate,
6-chloro-3,4-xylenyl-N-methyl carbamate,
4-methylthio-3,5-xylenyl-N-methyl carbamate,
N-methyl-1-naphthylcarbamate,
N-ethyl-1-naphthylcarbamate,
N-isopropyl-1-naphthylcarbamate,
N-butyl-1-naphthylcarbamate,
N-hexyl-1-naphthylcarbamate,
1-(4-chloro-1-naphthenyl)-N-methyl carbamate,
1-(5,6-dihydronaphthyl)-N-methyl carbamate,
1-(5,8-dihydronaphthyl)-N-methyl carbamate,
4-benzothienyl-N-methyl carbamate,
1-phenyl-3-methylpyrazol-5-yl-N,N-dimethyl carbamate,
2-(N,N-dimethylcarbamyl)-3-methylpyrazol-5-yl-N,N-dimethyl carbamate,
3,4-xylyl-N-methylcarbamate,
3-methyl-5-isopropylphenyl-N-methylcarbamate,
2-chlorophenyl-N-methylcarbamate, and
2,2-dimethyl-1,3-benzodioxol-4-yl-N-methylcarbamate.

The preferred carbamates are 2-isoproxyphenyl-N-methylcarbamate, commonly known as propoxur or Sendran TM and N-methyl-1-naphthylcarbamate, commonly known as carbaryl or Sevin TM.

The carbamates of Formula I and methods for their preparation have been described in U.S. Pat. Nos. 2,903,478; 3,111,539 and 3,203,853.

In the preparation of the plasticized thermoplastic component of the present invention, there can be employed any suitable thermoplastic resin which is satisfactorily compatible with the plasticizer employed, naled and the carbamates. The various known synthetic resins which can be used for a pet collar containing the combination of insecticides of this invention include materials such as polyethylene, polypropylene, copolymers of ethylene and propylene, nylon, cellophane, polyacrylates such as polymers and copolymers of methylacrylate, ethylacrylate, methylmethacrylate and ethylmethacrylate, polymers of vinyl compounds such as polystyrene, polymerized divinylbenzene, polyvinylhalogenides, such as polyvinylchloride; polyvinylacetals, such as polyvinylbutyral; polyvinylidene compounds such as polyvinylidenechloride, polyvinylacetate, ethylvinylacetate-vinylacetate copolymers; copolymers of vinylchloride and vinylacetate, polyurethanes, polyaldehydes, and thermoplastics.

Polyvinylchloride (PVC) homopolymers and copolymers with other polymers such as polyvinyl acetate (PVA) are preferred synthetic resin materials. Suitable PVC resins are commercially available and include, for example, PVC homopolymer dispersion resin Firestone FPC-6337 TM available from Firestone Plastics Co. and PVC homopolymer extender resin Borden 260S TM available from the Borden Co. and mixtures thereof. Other suitable, commercially available PVC resins are known in the art. Suitable PVC-PVA copolymers are also commercially available and include, for example, Geon 135 (Goodrich Corp.), PVC-74 (Diamond Alkali Co.) and XR-6333 (Exxon-Firestone). Other PVC-PVA copolymers are also known in the art.

The preparation of synthetic resin-insecticide combinations is achieved by conventional methods. Because of the compatibility of naled and the carbamates in the resin dispersions, the compositions may be prepared merely by mechanically mixing of the insecticides with powdered resin. Fluid pastes, or plastisol dispersions, can be made which, as is known, can be molded, extruded, cast, or otherwise formed into the shape of a band or strip. Where the prepolymerized resin exists in liquid form, as in the case of such monomers as styrene or methyl methacrylate, the insecticides may be incorporated in the liquid before it is polymerized or cured. The term "dispersion" as used herein is intended to include mixtures of a solid with a liquid, a liquid with a liquid and a solid with a solid.

In the embodiments where polyvinyl resins are used, plasticizers and other additives commonly used for providing the flexibility, strength and surface characteristics desired for a pet collar are well known to those skilled in this art, and no further discussion is deemed necessary here. In addition, coloring and odor control agents may be employed in the collars of the present invention to enhance consumer acceptance.

Plasticizers suitable for preparing the plasticized thermoplastic resin component of the compositions of the present invention are those conventionally employed in plasticizing solid thermoplastic resins. The particular plasticizer or plasticizers employed will depend upon the resin and its compatability therewith. Suitable plasticizers include esters of phosphoric acid such as tricresyl phosphate and esters of phthalic acid such as dioctyl phthalate. Other esters such as those of adipic acid, azalaic acid, maleic acid, ricinoleic acid, myristic acid, and trimellitic acid as well as complex linear polyeters, polymeric plasticizers and epoxidized soybean oils.

Other ingredients such as stabilizers, lubricants, fillers and coloring materials can be included in the compositions of the present invention without changing fundamental properties thereof. Suitable stabilizers are the antioxidants and agents which protect the resin from ultraviolet radiation, undue degradation during processing such as casting and extrusion, a wide variety of which are commercially available.

Some stabilizers such as epoxidized soybean oils or epoxidized octyl tallate serve also as a secondary plasticizer. Stearates including stearic acid and low molecular weight polyethylene are examples of lubricants which can be used.

Because of the low vapor pressure of naled, which is believed responsible for a relatively low release rate, the naled release rate from PVC-naled-carbamate collars is enhanced by the use of an additive in the dispersion. This makes possible effective flea control at lower initial naled concentrations and a collar having an increased effective life.

The additive, also referred to as a surface porosity control component, is present in the final plastisol dispersion or mix used in forming the collar, and hence must be non-reactive with the other components of the dispersion or mix. The main function of the additive is to provide a surface porosity which preferably includes pores extending part way into the body of the collar. The desired surface characteristics are obtained by the vaporization of the additive during the curing period. Hence the additive should comprise one or more compounds having a boiling point at or below the curing temperature of the resin.

Compounds which are suitable as the surface porosity control component in PVC resins which are cured at a temperature in the range of between about 300° to 375° F. include aldehydes and their lower alkyl acetals containing bromine or chlorine. The porosity control component may thus include one or more of the following which have approximate boiling point temperature as set forth:

| Name | B.P. °F. |
|---|---|
| chloroacetaldehyde | 185 |
| dichloroacetaldehyde | 192 |
| chloral | 218 |
| bromoacetaldehyde | 176–221 |
| dibromoacetaldehyde | 288 |
| bromal | 346 |
| bromodichloroacetaldehyde | 258 |
| chlorodibromoacetaldehyde | 299 |
| bromochloroacetaldehyde | 233 |
| 2-bromopropanol | 229 |

The surface porosity control component is included in the synthetic resin-naled-carbamate combination in an amount sufficient to produce surface porosity by its vaporization during curing of the dispersion whereby said cured strip releases naled gas at a rate effective to control fleas throughout a period of at least about 90 days without forming droplets on the strip. While the amount of the porosity control component to be used depends on the density of surface openings desired and somewhat on the particular procedure used for curing the resin, it is generally from about 0.8 to 4, preferably from about 1 to 3 wt. percent of the dispersion.

The invention is illustrated by the following Examples which are to be considered as illustrative of the present invention. It should be understood, however, that the invention is not limited to the specific details of the Examples.

EXAMPLE 1

A mixture in parts by weight of

| | |
|---|---|
| 35.82 | PVC homopolymer dispersion Resin Type A (Firestone FPC-6337™) |
| 17.32 | PVC homopolymer extender Resin Type B (Borden 260S™) |
| 16.36 | di-2-ethylhexylphthalate |
| 2.36 | epoxidized octyl tallate |
| 0.94 | calcium and zinc stearate powders |
| 19.90 | naled (dimethyl 1,2-dibromo-2,2-dichloroethyl phosphate |
| 2.30 | surface porosity control component (e.g. bromodichloroethylphosphate) |
| 5.00 | 2-isopropoxyphenyl N-methylcarbamate (90%) and amorphous silica (10%) in dust form |
| 100.00 | total | was thoroughly triturated to form a plastisol. A portion of the plastisol was metered to a machined aluminum open-faced cast mold having a cavity ⅜" in width×21" in length×⅛" in depth. Temperature of the mold at filling time was approximately 200° F. The mold was immediately placed in an oven and heated to 310°–335° F. by means of hot air and radiant heat. The mold containing the dispersion was moved through the oven over a 6 minute period. Thus, the dispersion was maintained at or above the curing temperature of 310°-335° F. for about 6 minutes. Cooling was then started, the temperature being lowered rapidly to 305° F. within 30 seconds. The cured strip was immediately thereafter removed from the mold and cooled rapidly to room temperature. The top side of the collar was rounded due to the meniscus formed on filling the mold, the shape being retained during curing.

Analysis of the collar after curing and cooling showed the naled (dimethyl 1,2-dibromo-2,2-dichloroethyl phosphate) content of the collar to be 17.9 weight % and the 2-isopropoxyphenyl-N-methyl carbamate content to be 4.4 weight %.

EXAMPLE 2

A mixture in parts by weight of

| | |
|---|---|
| 34.19 | PVC homopolymer dispersion Resin Type A (Firestone FPC-6337$^{TM}$) |
| 16.54 | PVC homopolymer extender Resin Type B (Borden 260S$^{TM}$) |
| 15.62 | di-2-ethylhexylphthalate |
| 2.25 | epoxidized octyl tallate |
| 0.90 | calcium and zinc stearate powders (50-50 by wt.) |
| 19.90 | naled (dimethyl 1,2-dibromo-2,2-dichloroethyl phosphate) |
| 2.30 | surface porosity control component (e.g. bromo-dichloroacetaldehyde) |
| 8.30 | 2-isopropoxyphenyl N-methylcarbamate (90%) and amorphous silica (10%) in dust form |
| 100.00 | total | was thoroughly triturated to form a plastisol. A portion of the plastisol was molded into a collar ⅜"×21"×⅛" thickness as in Example 1. Analyses of the collar after curing and cooling showed the content of dimethyl 1,2-dibromo-2,2-dichloroethyl phosphate to be 18.3 weight % and the 2-isopropoxyphenyl N-methyl carbamate content to be 7.4 weight %.

EXAMPLE 3

A mixture in parts by weight of

| | |
|---|---|
| 37.00 | PVC homopolymer dispersion Resin Type A (Firestone FPC-6337$^{TM}$) |
| 17.90 | PVC homopolymer extender Resin Type B (Diamond 7-44L$^{TM}$) |
| 17.58 | di-2-ethylhexylphthalate |
| 2.44 | epoxidized octyl tallate |
| 0.98 | calcium and zinc stearate powders (50-50 by wt.) |
| 17.55 | naled (dimethyl 1,2-dibromo-2,2-dichloroethyl phosphate) |
| 1.95 | surface porosity control component |
| 4.60 | N-methyl-1-naphthylcarbamate |
| 100.00 | total | was thoroughly triturated to form a plastisol. A portion of the plastisol was molded into a collar ⅜"×21"×⅛" thickness as in Example 1. Analysis of the collar after curing and cooling showed the content of dimethyl 1,2-dibromo-2,2-dichloroethyl phosphate to be 15.0 weight % and the content of 1-naphthyl-N-methyl carbamate to be 4.2 weight %.

COMPARATIVE EXAMPLE 1

Following the procedure of Example 1 and using a plastisol dispersion consisting in parts by weight of

| | |
|---|---|
| 35.62 | PVC homopolymer dispersion Resin Type A (Firestone FPC-6337$^{TM}$) (a) |
| 17.23 | PVC homopolymer extender Resin Type B (Borden 260S$^{TM}$) (b) |
| 16.27 | di-2-ethylhexyphthalate (DOP) |
| 2.34 | epoxidized octyl tallate (EPO) |
| 0.94 | calcium and zinc stearate powders (50-50 by wt.) |
| 27.60 | naled (dimethyl 1,2-dibromo-2,2-dichloroethyl phosphate) |
| 100.00 | total | was thoroughly triturated to form a plastisol. A portion of the plastisol was molded into a collar ⅜"×21"×⅛" thickness. Analysis of the collar after curing and cooling showed the content of dimethyl 1,2-dibromo-2,2-dichloroethyl phosphate to be 22 weight %.

COMPARATIVE EXAMPLE 2

Following the procedure of Example 1, a mixture in parts by weight of

| | |
|---|---|
| 38.3 | PVC homopolymer dispersion Resin Type A (Firestone FPC-6337$^{TM}$) |
| 18.5 | PVC homopolymer extender Resin Type B (Diamond PVC-7-44L$^{TM}$) |
| 18.7 | di-2-ethylhexylphthalate |
| 2.5 | epoxidized octyl tallate |
| 1.0 | calcium and zinc stearate powders (50-50 by wt.) |
| 21.0 | naled (dimethyl 1,2-dibromo-2,2-dichloroethyl phosphate) |
| 100.0 | total | was thoroughly triturated to form a plastisol. A portion of the plastisol was molded into a collar ⅜"×21"×⅛" thickness as in Example 1. Analysis of the collar after curing and cooling showed the content of dimethyl 1,2-dibromo-2,2-dichloroethyl phosphate to be 16 weight %.

EXAMPLE 4

A mixture in parts by weight of

| | |
|---|---|
| 36.05 | PVC homopolymer dispersion Resin Type A (Firestone FPC-6337$^{TM}$) |
| 17.44 | PVC homopolymer extender Resin Type B (Borden 260S$^{TM}$) |
| 16.88 | di-2-ethylhexylphthalate |
| 2.36 | epoxidized octyl tallate |
| 0.88 | calcium and zinc stearate powders (50-50 by weight) |
| 19.25 | naled (dimethyl 1,2-dibromo-2,2-dichloroethyl phosphate |
| 2.14 | surface porosity control component (e.g., bromo-dichloroacetaldehyde) |
| 5.00 | 2-isopropoxyphenyl-N-methyl carbamate 90% and amorphous silica 10 |
| 100.00 | total | was thoroughly triturated to form a plastisol. A portion of the plastisol was molded into a collar ⅜"×21"×⅛" thickness as in Example 1. Analysis of the collar after molding and curing showed the dimethyl 1,2-dibromo-2,2-dichloroethyl phosphate content to be 16.2 weight % and the 2-isopropoxyphenyl-N-methyl carbamate content to be 4.2 weight %.

EXAMPLE 5

A mixture in parts by weight of

| | |
|---|---|
| 42.33 | PVC homopolymer dispersion Resin Type A (Firestone FPC 6337™) |
| 20.47 | PVC homopolymer extender Resin Type B (Borden 260S™) |
| 19.81 | di-2-ethylhexylphthalate |
| 2.77 | epoxidized octyl tallate |
| 1.04 | calcium and zinc stearate powders (50–50 by weight) |
| 9.70 | naled (dimethyl 1,2-dibromo-2,2-dichloroethyl phosphate) |
| 1.08 | surface porosity content component (e.g., dibromoacetaldehyde) |
| 2.80 | 2-isopropoxyphenyl-N-methyl carbamate 90% and amorphous silica 10% |
| 100.00 | total | was thoroughly triturated to form a plastisol. A portion of the plastisol was molded into a collar ⅜"×21"×⅛" thickness as in Example 1. Analysis of the collar after moulding and curing showed the dimethyl 1,2-dibromo-2,2-dichloroethyl phosphate content to be 7.0 weight % and the 2-isopropoxyphenyl-N-methyl carbamate content to be 2.4 weight %.

EXAMPLE 6

A mixture in parts by weight of

| | |
|---|---|
| 40.73 | PVC homopolymer dispersion Resin Type A (Firestone FPC 6337™) (a) |
| 19.70 | PVC homopolymer extender Resin Type B (Diamond PVC-7-44L™) (f) |
| 19.36 | di-2-ethylhexylphthalate (DOP) |
| 2.68 | epoxidized octyl tallate (EPO) (c) |
| 1.08 | calcium and zinc stearate powders (c) (50–50 by weight) |
| 12.75 | naled (dimethyl 1,2-dibromo-2,2-dichloroethyl phosphate) |
| 3.70 | 1-naphthyl-N-methyl carbamate (97.5% active) |
| 100.00 | total | was thoroughly triturated to form a plastisol. A portion of the plastisol was molded into a collar ⅜"×21"×1/9" thickness as in Example 1. Analysis of the collar after curing and cooling showed the content of dimethyl 1,2-dibromo-2,2-dichloroethyl phosphate to be 10.0 weight % and the content of 1-naphthyl-N-methyl carbamate to be 3.5 weight %.

Insecticidal Efficacy of Collars

The insecticidal efficacy of the animal collars of the present invention was determined using animals confined to cages wearing various collars. The animals were infested with fleas or ticks on the same day the collar was applied to the animal and periodically thereafter. The number of surviving fleas were counted after each infestation. Control animals wore collars containing only naled (dimethyl 1,2-dibromo-2,2-dichloroethyl phosphate).

Three groups of dogs (6 dogs per group) were provided with collars from Example 1, Example 2 and Comparative Example 1. Each dog was infested with 50 fleas (Ctenocephalides felis) biweekly for a total of nine infestations. Flea counts were made at days 1, 3 and 5 post infestation. The data in Table 1 shows a 63–66% greater reduction in flea content on animals wearing the collars of the present invention during the first nineteen days of the test period. The number of fleas present each day was counted.

The data in Table 2 shows the results of the entire test period with a 26–57% greater reduction in flea content on animals wearing the collars to the present invention. The dead fleas were counted in the pans beneath the cage of each dog on days 1–5 after each infestation.

Table 1

| | Average No. of Residual Fleas/Dog | | |
|---|---|---|---|
| [1]Day | Example 1 | Example 2 | Comparative Example 1 |
| 0 | — | — | — |
| 1 | 1.17 | 0.83 | 6.83 |
| 3 | 0.83 | 1.00 | 2.17 |
| 5 | 0.33 | 0.0 | 3.17 |
| 14 | — | — | — |
| 15 | 1.83 | 3.67 | 3.50 |
| 17 | 1.83 | 1.17 | 3.50 |
| 19 | 1.00 | 1.17 | 1.83 |
| | 6.99 total | 7.84 total | 21.00 total |

[1]Dogs infested at day 0 and day 14.

Table 2

| Day | | Average No. of Dead Fleas/Dog | | |
|---|---|---|---|---|
| Infestation | Count | Example 1 | Example 2 | Comparative Example |
| 0 | 1–5 | [1]22 22.3 | 16.7 | |
| 14 | 15–19 | 24.3 | 17.7 | 20.2 |
| 28 | 29–33 | 22.0 | 20.5 | [1]17.0 |
| 42 | 43–47 | 19.7 | 9.8 | 14.3 |
| 56 | 57–61 | 17.0 | 16.2 | 10.7 |
| 70 | 71–75 | 16.5 | 15.2 | 6.2 |
| 84 | 85–89 | 16.3 | 16.3 | 11.2 |
| 84 | 99–103 | 19.2 | 14.5 | 8.5 |
| 112 | 113–117 | 20.0 | 9.3 | 8.0 |
| | | 177.0 total | 141.3 total | 112.8 total |

[1]Estimated; pans cleaned inadvertently.

In another comparative test, 9 individual dogs were fitted with collars from Example 4, and 3 individually caged dogs were fitted with collars from Comparative Example 2. The dogs were infested at days 0, 14 and 29 with 50 fleas per dog (Ctenocephalides felis). The number of residual fleas per dog was determined on various days post infestation. The data are shown in Table 3.

Table 3

| | Average No. of Residual Fleas/Dog | |
|---|---|---|
| Day | Example 4 | Comparative Example 2 |
| 0 | — | — |
| 2 | 2.89 | 4.67 |
| 4 | 0.56 | 2.0 |
| 6 | 0.0 | 0.0 |
| 10 | 0.44 | 2.0 |
| 14 | — | — |
| 16 | 0.67 | 1.0 |
| 18 | 0.22 | 0.67 |
| 21 | 0.11 | 0.0 |
| 24 | 0.11 | 0.67 |
| 28 | 0.0 | 0.33 |
| 29 | — | — |
| 30 | 1.89 | 1.0 |
| 32 | 1.11 | 2.0 |
| 35 | 1.0 | 2.0 |
| 38 | 0.67 | 1.0 |
| 42 | 0.11 | 1.0 |

Table 3-continued

| | Average No. of Residual Fleas/Dog | |
|---|---|---|
| Day | Example 4 | Comparative Example 2 |
| | 9.89 Total | 18.34 Total |

The efficacy of the collars of the present invention were tested on dogs infested with brown dog ticks (Rhipecephalus sanguineus). The number of residual live ticks and the number of live attached ticks per individual dog was determined per post infestation days. Each dog was infested with 50 ticks at days 0, 14 28 and 42. The tick counts were made on days 1, 3, 5 and 14 post infestation. The data are shown in Table 4.

Table 4

| | No. Live Residual Ticks | | No. Live Attached Ticks | |
|---|---|---|---|---|
| Days | Example 4 | Comparative Example 2 | Example 4 | Comparative Example 2 |
| 0–14 | 43.8 | 63.9 | 33.9 | 47.2 |
| 16–28 | 36.6 | 59.3 | 24.8 | 47.3 |
| 30–42 | 28.5 | 43.8 | 22.5 | 36.8 |
| 44–56 | 33.4 | 27.0 | 23.4 | 6.9 |
| | 142.3 | 194.0 | 94.6 | 138.2 |

SUMMARY OF ADVANTAGES

The pet collars of the present invention have the advantage of the release of both a vaporous insecticide and a substantially non-volatile powdery insecticide. The naled vapor releases to the atmosphere surrounding the pet and the carbamate powder migrates onto the surface of the collar and then onto the coat of the animal.

The resin-naled-carbamate pet collars of the present invention have improved naled release over pet collars containing only naled. The net effect of increased naled release and the migration of the carbamate onto the collar and from the collar surface onto the coat of the animal is a more effective collar against the infestations of fleas and ticks.

The pet collars containing the combination of naled and carbamate provide greater protection against ticks than naled alone, particularly on free running animals where the naled vapor is released to unconfined space. The carbamate as a powder is distributed on the animal coat and more effectively controls the ticks and results in a larger percentage kill.

The present invention may be embodied in other specific forms without departing from the spirit or essential characteristics thereof. The presently disclosed embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed and intended to be covered by Letters Patent is:

1. A flea and tick control collar for a warm-blooded animal comprising:
a strip of flexible plasticized polyvinyl chloride containing between about 5 to 20 weight % of dimethyl 1,2-dibromo-2,2-dichloroethyl phosphate and about 2 to about 12 weight % of a substantially non-volatile carbamate insecticide and having a width, thickness and length sufficient to encircle the neck of the animal with clamping means at one end of the collar for engaging a spaced collar portion to prevent loss of the collar from the neck of the wearing animal; said strip being formed from a dispersion of plasticized polyvinyl chloride, dimethyl 1,2-dibromo-2,2-dichloroethyl phosphate, a substantially non-volatile carbamate and a surface porosity control component selected from the group consisting of chloroacetaldehyde, dichloroacetaldehyde, chloral, bromoacetaldehyde, dibromoacetaldehyde, bromal, bromodichloroacetaldehyde, chlorodibromoacetaldehyde, bromochloroacetaldehyde, 2-bromopropanol and mixtures thereof, said dispersion being heated to its curing temperature to produce surface openings in communication with pores in said strip by vaporization of said porosity control component to provide for release of dimethyl 1,2-dibromo-2,2-dichloroethyl phosphate gas and said carbamate at a rate effective to control fleas and ticks on said animal throughout a period of at least about 90 days.

2. The flea and tick collar of claim 1 wherein the carbamate is selected from those having the formula:

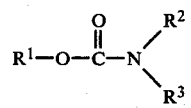

wherein;
$R^1$ is phenyl, substituted phenyl, naphthyl, substituted naphthyl, heterocyclic or substituted heterocyclic,
$R^2$ is hydrogen or lower alkyl, and
$R^3$ is lower alkyl.

3. The flea and tick collar of claim 2 wherein the carbamate is 2-isopropoxyphenyl-N-methyl carbamate.

4. The flea and tick collar of claim 2 wherein the carbamate is 1-naphthyl-N-methyl carbamate.

5. A method of controlling infestations of ticks and fleas on dogs or cats which comprises:
providing a strip having a width and thickness and length suitable for use as a collar for said dog or cat, said strip comprising a mixture of plasticized polyvinyl chloride and from between 5 to 20 weight % of dimethyl 1,2-dibromo-2,2-dichloroethyl phosphate and from about 2 to about 12 weight % of a substantially non-volatile carbamate insecticide; said strip being formed from a dispersion of said plasticized polyvinyl chloride, dimethyl 1,2-dibromo-2,2-dichloroethyl phosphate and said substantially non-volatile carbamate, and a minor amount of a surface porosity control agent selected from the group consisting of chloroacetaldehyde, dichloroacetaldehyde, chloral, bromoacetaldehyde, dibromoacetaldehyde, bromal, bromodichloroacetaldehyde, chlorodibromoacetaldehyde, bromochloroacetaldehyde, 2-bromopropanol and mixtures thereof, said dispersion being formed into said strip at the curing temperature of said dispersion to vaporize said surface porosity control agent and produce surface porosity in said strip to provide for release of dimethyl 1,2-dibromo-2,2-dichloroethyl phosphate as a vapor and said carbamate as a powder at a rate to effectively control ticks and fleas while on said dog or cat throughout a period of at least about 90 days but insufficient to be toxic to said dog or cat; providing on said collar near one end of clamping means for engaging a spaced collar portion to prevent loss of the collar from the next of said dog or cat; and placing and maintaining said collar on said dog or cat.

6. The method of claim 5 wherein the carbamate is 2-isopropoxyphenyl-N-methyl carbamate.

7. The method of claim 5 wherein the carbamate is 1-naphthyl-N-methyl carbamate.

* * * * *